(12) United States Patent
Lippert et al.

(10) Patent No.: US 9,664,620 B2
(45) Date of Patent: May 30, 2017

(54) MICROSCOPE

(71) Applicant: Carl Zeiss Microscopy GmbH, Jena (DE)

(72) Inventors: Helmut Lippert, Jena (DE); Thomas Kalkbrenner, Jena (DE); Ingo Kleppe, Jena (DE); Ralf Wolleschensky, Jena (DE)

(73) Assignee: Carl Zeiss Microscopy GmbH, Jena (DE)

(*) Notice: Subject to any disclaimer, the term of this patent is extended or adjusted under 35 U.S.C. 154(b) by 0 days.

(21) Appl. No.: 14/413,806

(22) PCT Filed: Jun. 11, 2013

(86) PCT No.: PCT/EP2013/061999
§ 371 (c)(1),
(2) Date: Jan. 9, 2015

(87) PCT Pub. No.: WO2014/009080
PCT Pub. Date: Jan. 16, 2014

(65) Prior Publication Data
US 2015/0226670 A1    Aug. 13, 2015

(30) Foreign Application Priority Data

Jul. 9, 2012    (DE) .................. 10 2012 211 943

(51) Int. Cl.
*G02B 21/06*    (2006.01)
*G01N 21/64*    (2006.01)
(Continued)

(52) U.S. Cl.
CPC ..... *G01N 21/6458* (2013.01); *G02B 21/0032* (2013.01); *G02B 21/0048* (2013.01);
(Continued)

(58) Field of Classification Search
CPC ............ G02B 21/0032; G02B 21/0076; G02B 21/10; G02B 21/06; G02B 21/16;
(Continued)

(56) References Cited

U.S. PATENT DOCUMENTS

| | | |
|---|---|---|
| 6,064,518 A | 5/2000 | Stelzer et al. |
| 8,362,448 B2 | 1/2013 | Wolleschensky et al. |

(Continued)

FOREIGN PATENT DOCUMENTS

| | | |
|---|---|---|
| DE | 196 32 040 | 2/1998 |
| DE | 198 34 279 | 3/2000 |

(Continued)

OTHER PUBLICATIONS

C. Dunsby: "Optically sectioned imaging by oblique plane microscopy". In: Optics Express, vol. No. 16, Dec. 2008 pp. 20306-20316.
(Continued)

*Primary Examiner* — Bumsuk Won
*Assistant Examiner* — Balram Parbadia
(74) *Attorney, Agent, or Firm* — Frommer Lawrence & Haug LLP (57) ABSTRACT

A microscope including a sample carrier configured to support a sample. Excitation light illuminates the sample via an excitation beam path, Detection light from the sample is guided to detection means via a detection beam path. Through an objective arranged along the optical axis, excitation light is guided in direction of the sample carrier and detection light coming from the sample is guided in direction of the detection means. Beam-splitting means separate excitation light and detection light. Also provided are means for generating a light sheet from excitation light, and means for illuminating the sample with this light sheet. The light sheet lies in a plane at a nonzero angle to the optical axis. The means for illuminating the sample include an optical-
(Continued)

deflecting device arranged on or at the sample carrier, which deflects excitation light from the objective into the plane of the light sheet via an optically active surface.

19 Claims, 4 Drawing Sheets

(51) Int. Cl.
G02B 21/16 (2006.01)
G02B 21/36 (2006.01)
G02B 21/00 (2006.01)
G02B 21/26 (2006.01)

(52) U.S. Cl.
CPC ............ *G02B 21/06* (2013.01); *G02B 21/16* (2013.01); *G02B 21/26* (2013.01); *G02B 21/367* (2013.01); *G01N 2201/02* (2013.01); *G01N 2201/06113* (2013.01)

(58) Field of Classification Search
CPC .... G02B 21/00; G02B 21/0064; G02B 21/18; G02B 21/26; G02B 26/08; G01N 21/6458
See application file for complete search history.

(56) References Cited

U.S. PATENT DOCUMENTS

| | | | |
|---|---|---|---|
| 2003/0076587 | A1 | 4/2003 | Stelzer et al. |
| 2003/0232427 | A1* | 12/2003 | Montagu ............ G01N 21/6428 435/287.2 |
| 2005/0111092 | A1 | 5/2005 | Kitamura et al. |
| 2005/0211874 | A1* | 9/2005 | Takeyama ............ G02B 21/16 250/208.1 |
| 2006/0012855 | A1 | 1/2006 | Wolleschensky |
| 2006/0250928 | A1* | 11/2006 | Yamashita ............... G02B 7/14 369/100 |
| 2008/0030850 | A1 | 2/2008 | Wolleschensky |
| 2011/0036996 | A1 | 2/2011 | Wolleschensky et al. |
| 2011/0182529 | A1* | 7/2011 | Kempe ............ G01N 21/6458 382/274 |
| 2012/0098949 | A1* | 4/2012 | Knebel ................ G02B 21/002 348/79 |
| 2012/0200905 | A1* | 8/2012 | Paulus ................ G02B 21/025 359/230 |

FOREIGN PATENT DOCUMENTS

| | | |
|---|---|---|
| DE | 10 2004 034 957 | 2/2006 |
| DE | 10 2008 009 216 | 8/2009 |
| DE | 20 2011 110 077 | 1/2013 |
| EP | 1617274 | 1/2006 |
| JP | 9-236751 | 9/1997 |
| JP | 2000-509842 | 8/2000 |
| JP | 2002-521733 | 7/2002 |
| JP | 2006-030991 | 2/2006 |
| JP | 2006-030992 | 2/2006 |

OTHER PUBLICATIONS

Christoph J. Engelbrecht et al.: "Miniaturized selective plane illumination microscopy for high-contrast in vivo fluorescence imaging". In: Optics Letters, 35, May 1, 2010, vol. No. 9, pp. 1413-1415.
Joerg G. Ritter et al.: Light Sheet Microscopy for Single Molecule Tracking in Living Tissue. In: PLoSONE, 5, Jul. 2010, 7: e11639, 1-9. [doi:1 0.1371/journal.pone,011639].
Philipp J. Keller et al.: "Fast, high-contrast imaging of animal development with scanned light sheet-based structured-illumination microscopy". In: Nature Methods, 7, 2010, 8, 637-642. [doi:10. 1038/nmeth.1476].
Sunil Kumar et al. : High-speed 2D and 3D fluorescence microscopy of cardiac myocytes. In: Optics Express, 19, Jul. 2011,15,13839-13847.
Terrence F. Holekamp et al.: "Fast Three-Dimensional Fluorescence Imaging of Activity in Neural Populations by Objective-Coupled Planar Illumination Microscopy". In: Neuron, 57, Mar. 2008, 661-672. [doi:10.1016/j.neuron.2008.01 .011].
Thomas A Planchon et al.: "Rapid three-dimensional isotropic imaging of living cells using Bessel beam plane illumination". In: Nature Methods, 8, 2011, 5, 417-423. [doi:1 0.1 038/nmeth.1586].
Sunil Kumar et al: "Optically sectioned imaging by oblique plane microscopy", Three-Dimensional and Multidimensional Microscopy: Image Acquisition and Processing XVIII, SPIE vol. 7904, Feb. 2011 pp. 1-4, XP060007356, DOI: 10.1117/12.873471.
Notification of Transmittal of Translation of the International Preliminary Report on Patentability dated Jan. 13, 2015.
International Search Report for Application No. PCT/EP2013/ 061999 dated Aug. 14, 2013.
German Search Report for Application No. 10 2012 211 943.4 dated Mar. 26, 2014.

* cited by examiner

MICROSCOPE

The present application claims priority from PCT Patent Application No. PCT/EP2013/061999 filed on Jun. 11, 2013, which claims priority from German Patent Application No. DE. 10 2012 211 943.4 tiled on Jul. 9, 2012 ,the disclosures of which are incorporated herein by reference in their entirety.

FIELD OF THE INVENTION

The invention is directed to a microscope. A microscope of this type comprises a sample stage with a stage surface in a stage plane that forms an angle different Chan zero to an optical axis Z. Arranged on the sample stage, preferably no as to be secured against unintentional displacement, is a sample carrier on which a sample is supported. The microscope further comprises an excitation beam path via which the sample is illuminated with excitation light and a detection beam path via which detection light coming from the sample is directed to detection means. The detection means comprise, for example, a camera or a pixel array or other recording equipment suitable for image data acquisition. An evaluating unit which evaluates the image data is generally also connected to the image acquisition means. The microscope further comprises an objective which is arranged along the optical axis Z and through which excitation light is guided in direction of the sample stage and detection light coming from the sample is guided in direction of the detection means. The excitation light and the detection light can be split by beam splitting means in the microscope such that they are divided into different beam paths. Finally, the microscope also comprises means for generating a light sheet or a quasi light sheet—i.e., a light sheet that is generated by scanning with a point-shaped or line-shaped beam—from excitation light and means for illuminating the sample with this light sheet. The light sheet lies in a plane which forms an angle different than zero to the optical axis Z.

It is noted that citation or identification of any document in this application is not an admission that such document is available as prior art to the present invention.

In recent years, the illumination of samples with a light sheet whose plane intersects the optical axis at an angle different than zero has gained increasing importance for the study of biological samples. Generally, the light sheet forms a right angle with the detection direction which usually corresponds to the optical axis of the microscope objective. This technology is also referred to as SPIM (selective/single-plane illumination microscopy). SPIM technology has also been used for some time in fluorescence microscopy, in which case it is referred to as LSFM (light sheet fluorescence microscopy). LSFM technology has a number of advantages over other established methods such as confocal laser scanning microscopy or two-photon microscopy. Since detection can be carried out in the far field, larger sample areas can be detected. Although the resolution is somewhat lower than in confocal laser scanning microscopy and two-photon microscopy, thicker samples may be analyzed with LSFM technology. Beyond this, light stress and bleaching of the samples is minimized with this method because the sample is only illuminated by a thin light sheet. Further, optical sections from which three-dimensional images can be reconstructed can be produced with the LSFM method without special effort.

Heretofore, the availability of commercial microscopes suitable for SPIM or LSFM has been limited so that individual research groups generally developed their own creations. However, the basic principle is the same in all of these arrangements. Usually, a laser is used to generate the light sheet for light sheet fluorescence microscopy. The light sheet is shaped and directed through an illumination objective onto the sample by means of special optical elements, for example a cylindrical lens. The light sheet is actually not completely planar but rather has a finite thickness which is thinnest at the focal point of the illumination objective and increases toward the edges. Usually, the focal point, i.e., the thinnest area of the Light sheet, is positioned in the center of a sample chamber. For this purpose, the sample chamber is constructed from optically transparent material and has at the top an opening through which the sample is placed in the chamber and can also be removed from the chamber, For example, the sample chamber may be filled with a gel on which dead sample material is supported or may be filled with a liquid suitable for receiving living cell material.

This arrangement of sample chamber, detection beam path and illumination beam path in relation to one another leads to complex, large-sited structures, which is one of the reasons why there are still no commercially available microscopes for SPIM technology. In particular, there has not yet been a commercial approach to integrate the methods in existing microscope systems. Further boundary conditions must be adhered to for fluorescence excitation which may not be carried out in the far field.

There are a number of known prior art arrangements of methods which are concerned with the advantageous use of SPIM technology for fluorescence microscopy or with. reducing the space occupied by the equipment in its entirety through particular technical solutions.

DE 10 2008 009 216 A1 describes an arrangement which is suitable for both photoactivation and photodeactivation (PALM method, photoactivated light microscopy) and for fluorescence excitation. In this case, the light sheet is generated by special optical means arranged in a conventional manner perpendicular to the detection direction and to the detection objective.

In the article "Rapid three-dimensional isotropic imaging of living cells using Bessel beam plane illumination" by Thomas A. Planchon et al., published online in *Nature Methods*, Mar. 4, 2011 (doi:10,1038/nmeth.1586), a method is described for illuminating living samples with light sheets which are formed from Bessel beams and which are especially thin in relation to their dimension in beam direction. Excitation and detection are carried out via two objectives which are arranged at a 90-degree angle to one another and which are partially surrounded by the sample chamber filled with liquid. To addition to these two objectives, a third, standard observation objective is also provided which allows an overview of the sample and which has an optical axis that intersects the optical axes of the two other objectives at a point and forms an angle of 45° and 135°,respectively, with these two other objectives.

The article "Fast, high-contrast imaging of animal development with scanned light sheet-based structured-illumination microscopy" by Philipp J. Keller et al., published online in *Nature Methods*, Jul. 4, 2010 (doi:10.1038/nmeth,1476), describes the generation of a "quasi light sheet" by means of a scanning mirror in relation to applications in fluorescence microscopy and for generating a structured illumination for contrast optimization. The modifier "quasi" denotes that the excitation beam is perceived not as a snapshot but as a light sheet over a period of time corresponding to the detection period.

The article "Miniaturized selective plane illumination microscopy (mini SPIM) for endoscopic high-contrast fluorescence imaging" by Christoph J. Engelbrecht et al, published in 2010 in *Optics Letters*, Apr. 28, 2010 (doi: 10.1364/OL.35.001413), describes an arrangement in which the illumination light is split into two beam paths, one of which serves for conventional illumination of the sample along the detection direction, while the other beam path is used for illuminating the sample with a light sheet perpendicular to the detection direction. The beams are guided respectively via fibers from the respective objectives in direction of the sample to a combined out-coupling piece, where the two beams are directed to the sample via corresponding out-coupling elements. A prism element which deflects the beam path from the detection direction by 90° is provided for coupling out the light sheet.

Also, in the method described in the article "Fast Three-Dimensional Fluorescence Imaging of Activity in Neural Populations by Objective-Coupled Planar Illumination Microscopy" by Terrence F. Holekamp et al., published in 2008 in *Neuron*, Volume 57, pages 661-672, the light sheet is generated via a fiber which in this case is fastened by a holder directly to the detection objective or holder thereof The fiber is displaced along the optical axis of the detection objective by means of piezo elements. In this way, the distance of the light sheet from the foremost lens of the detection objective can be varied so that optical sections can be generated in principle.

The article "Light sheet Microscopy for Single Molecule Tracking in Living Tissue" by Jörg G. Ritter, et al., published in *PLoS ONE* 5 (7): e11639, 2010, describes an arrangement for inverted microscopy which is particularly suitable for analyzing small samples.

DE 10 2004 034 957 A1 describes a special objective arrangement in which the light sheet is reflected in at the edge outside of the actual observation objective, for example, via imaging mirrors with a low numerical aperture. Mechanically, the surrounding mirror imaging the objective is a part of the objective in order to achieve the most homogeneous resolution possible, the reflecting optics cart be formed annularly, for example.

An arrangement in which a sample is likewise illuminated with a light sheet is described in the article "Optically sectioned imaging by oblique plane microscopy" by C. Dunsby, published in 2008 in *Optics Express* 16 (25), pages 20306-20316. In this case, however, illumination and detection are carried out through the same objective. Therefore, with respect to the optical axis of the excitation objective and detection objective, the plane of the light sheet is at a smaller angle, e.g., 60°,instead of 90°, to this optical axis. Because of the special construction, only small opposing areas of the objective can be used for illumination and detection, since otherwise the detection could not be carried out in a plane perpendicular to the light sheet plane.

A similar construction is also described in the article "High-speed 2D and 3D fluorescence microscopy of cardiac myocytes" by Sunil Kumar et al., published in 2011 in *Optics Express* 19 (15), pages 13839-13847. Here also, the same objective is used for detection and illumination with a light sheet; the light sheet is inclined with respect to the optical axis of the detection objective at an angle of appreciably less than 90°. With the aid of a second microscope, however, an intermediate image of the sample is generated, this intermediate image being imaged on a camera via a third microscope. The optical axis of the objective of the third microscope and second microscope form an angle different than zero. The illumination light is also beamed in simultaneously via the second microscope, and the illumination light therefore already forms a light sheet in the intermediate image. The light sheet plane and the optical axis of the objective of the third microscope form an angle of 90° to one another.

However, none of the arrangements described above allows a simple, unproblematic integration in exiting microscopes. Of course, the arrangement described by T. A. Planchon et al. can be used in the field of inverted microscopy in that a corresponding illumination-and-detection module comprising two objectives having optical axes which form an angle of 90° to one another is arranged above the object carrier or sample stage. But this arrangement also occupies a very large amount of space and is very costly because of the additional optics.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in US. Patent law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112), such that applicant(s) reserve the right to disclaim, and hereby disclose a disclaimer of, any previously described product, method of making the product, or process of using the product.

SUMMARY OF THE INVENTION

Therefore, it is the object of the invention to further develop a microscope of the type described in the introductory part which facilitates integration of SPIM technology in existing microscopes, particularly which facilitates the examination of small samples, particularly by fluorescence spectroscopy methods.

This object is met in a microscope of the type described above in that the means for illuminating the sample comprise at least one optical deflecting device which is arranged on or at the sample carrier and which is configured to deflect excitation light coining from the objective into the plane of the light sheet by means of at least one optically active surface. Whereas heretofore deflecting devices—using two different objectives for illumination and detection—were not provided at all or were arranged at the objective, the arrangement of at least one optical deflecting device at or on the sample carrier on the one hand allows the light sheet radiation to be decoupled from the illumination objective and detection objective as final optical element in the beam path before the sample so that a detection is possible over the entire aperture of the objective; on the other hand, as a result of this decoupling, conventional microscope objectives can be widely used without providing special holders or beam guiding means for the light sheet beam path. Arrangement at or on the sample carrier means that the at least one optical deflecting device can be detachably or permanently fastened to the sample carrier. However, it may simply be placed on the sample carrier without having a frictionally engaging or positively engaging connection therewith. Also, the at least one optical deflecting device can be fashioned integral with the sample carrier. The arrangement of the at least one optical deflecting device on the sample carrier also allows the use of a shared objective for illumination and detection while nevertheless generating a light sheet or quasi light sheet which forms an angle different than zero, generally a right angle, with the optical axis of the microscope objective through which the excitation light is guided to the sample or through which the detection light is guided from the sample, i.e., with the detection direction. To this end, the at least one optically active surface is correspondingly oriented, and corrections can be carried out via corresponding adjusting means, for example, a wobble plate, in the microscope.

For example, the optical deflecting device can be configured as a mirror element with at least one optically active surface formed as a mirror surface, the at least one mirror surface preferably forming an angle of 45° with the optical axis Z. Illumination light corning from the microscope objective which, for example, can excite fluorescence in certain fluorophores in the sample is guided to the mirror surface, where it is reflected in direction of the sample. The optical elements must be arranged in the excitation beam path such that the light sheet is formed substantially in the XY plane after reflection. This can be carried out through the use of anamorphic optical elements such as cylindrical lenses which are arranged at a corresponding location in the beam path, also in combination with the at least one optical deflecting device. However, it is particularly advantageous when the microscope is formed as a laser scanning microscope. The light sheet can then be generated as a quasi light sheet through the scanning means for point scanning which are available in this microscope. The light beam is guided linewise over the sample in quick succession through the movement of the scanning means, for example, the scanner mirror, such that effectively, or temporally and spatially averaged, the shape of a light sheet results.

While the configuration of the at least one optical deflecting device as a mirror element is particularly suited to microscopes in which the objective is arranged above the sample, i.e., also above the sample stage with the sample carrier, the at least one optical deflecting device is configured in another variant as a prism element with an optically active surface which is formed as inner side of a prism and which preferably forms an angle of 45° with optical axis Z. This variant is particularly suitable for use in inverted microscope stands in which excitation and detection take place below the sample stage, but can of course also be used with other stands. To this end, the at least one optical deflecting device is integrated in the stage or arranged at the latter such that it passes light corning from below Instead of a prism, a hollow cavity light guide can also be used, in which case the optically active surface is again mirrored. The light is then guided to the sample via a light output surface.

In another configuration, the optically active surface can also be comprised of a plurality of microprisms which on the average preferably form an angle of 45° with the optical axis Z. In this case and in the previous cases the angle can also deviate from 45' provided it is ensured via adjusting means that the propagation direction of the light sheet is substantially perpendicular to the detection direction. Accordingly, it is sufficient in principle when the angle deviates from zero, whereas an angle of 45° offers the advantage of a particularly simple orientation and, generally; no further adjusting means are necessary. The use of an optically active surface comprised of microprisms is advantageous in environments such as fluids which could otherwise contaminate planar mirror surfaces. This is prevented by microprisms; contact of the reflecting surface with the surrounding fluid or the sample is prevented.

The preferred configuration of the optically active surface with an angle of 45° to the optical axis Z is particularly relevant when the excitation light—in beam form—is guided parallel to the optical axis into or on the optically active surface of the optical deflecting device, which is advantageous because the numerical aperture For the excitation light is as high as possible. An optically active surface is then also generally sufficient in this case. However, this beam guidance is not absolutely necessary; and the light beam of the excitation light can also impinge on the optically active surface at an angle different than zero. Particularly when using prisms or microprisms for shaping the optically active surface, the principle of total reflection can also be utilized; for this purpose, when an optically active surface with an angle of 45° to the optical axis is used, a beam of excitation light impinging at an angle different than zero can be used or optical deflecting devices with more than one optically active surface which serve for beam deflection at shallower angles.

Optical deflecting devices in which the optically active surface is formed so as to surround the sample in a funnel-shaped manner are also suitable for inverted microscopy. For example, frustoconical caps with mirrored inner surfaces can be used in this case. These caps can be designed as disposable articles and have the advantage that the sample, if sufficiently small, can be completely surrounded such that the sample continues to be situated in a physiologically acting liquid which preserves its vital functions. Further, the cap can be displaced relatively easily on the sample carrier or sample stage or moved selectively in three spatial dimensions by means of special manipulation devices. The manipulation devices can also be used from the very start to position the caps on the sample from any direction.

In another arrangement, the at least one optical deflecting device is arranged at the sample carrier in that it is integrated directly therein as a funnel-shaped well. The illumination light is then deflected at the lateral walls of the funnel. For observing from above, the lateral walls are advantageously mirrored for observation. For inverted microscopy, the lateral walls take on the function of prism surfaces.

For the examination of very small samples on the magnitude of individual cells or cell clusters, it is advantageous when a plurality of optical deflecting devices are arranged on the sample carrier, preferably in the shape of a grid. This arrangement is possible, for example, for the funnel-shaped wells and also for the mirror elements or prism elements. The sample carrier can be designed, for example, as a multiwell plate, i.e., as a microtiter plate with a plurality of wells arranged in the shape of a grid. These wells can be funnel-shaped, for example, and accordingly form the optical deflecting devices.

However, the optical deflecting device can also be inserted into the wells before they are deposited there, or close the wells with the samples located therein in that after the sample is deposited they are placed on top in the manner of caps or covers.

In a further arrangement, the at least one optical deflecting device can be inserted from below relative to the sample carrier, preferably along the optical axis, into a corresponding opening of the sample carrier. This opening need not be present initially; but rather can be introduced first in the sample carrier also with the intermediary of the optical deflecting device. For example, the sample carrier can be provided with a grid of punch points at which an opening can be punched through the deflecting device. Depending on the type of sample and/or deflecting device, only one opening is punched, or a plurality of openings are punched. Analogously, the at least one deflecting device can also be introduced from above or obliquely from the side, also with the aid of the aforementioned manipulation. devices.

Further, the at least one optical deflecting device can also be detachably outfitted with a protective device which particularly protects the optically active surface during transporting. In case the samples are to be observed over a longer period of time or in case the samples are set up as cell cultures which must first develop naturally, or artificially accelerated these protective devices can also be left on the deflecting device or arranged separately for these processes. For example, they can be simple lids which are placed on the deflecting device, a removable foil, etc. The detachable connection can also be carried out by means of a clip closure so as to ensure that the protective device is retained in a reliable manner and penetration of liquid into the area of the optically active surface is prevented.

As has already been mentioned, adjusting means are preferably arranged in the beam path for adjusting the light sheet. These adjusting means can comprise a wobble plate, for example. Separate zoom optics can be arranged in the excitation beam path to vary the thickness of the light sheet. Further, collimation optics are preferably arranged in the excitation beam path so as to vary the position of the focus of the light sheet relative to the optical axis Z.

When the microscope is configured as a laser scanning microscope for point scanning, an axial displacement of the light sheet along the detection direction Z can be achieved in that the position of the sample carrier is displaced perpendicular to the scanning direction. In this way different planes of the sample can be scanned and an image stack can be generated for three-dimensional image evaluation. The same effect can be achieved when the position of the illumination beam is varied by means of further scanning means, e.g., a further scanning mirror, perpendicular to the scanning direction described above. Of course, the use of only one scanning means in different operating modes is also conceivable.

It will be appreciated that the features which are mentioned above and which will be described in the following can be used not only in the indicated combinations but also in other combinations or individually without departing from the scope of the present invention.

BRIEF DESCRIPTION OF THE DRAWINGS

FIGS. 2a), b) show how the illumination aperture can be adjusted by means of zoom optics;

FIGS. 4a)-d) show various configurations of sample carriers and/or optical deflecting devices.

FIGS. 5a)-c) show a further embodiment of the at least one optical deflecting device with an optically active surface as microprisms.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

Figure 1:
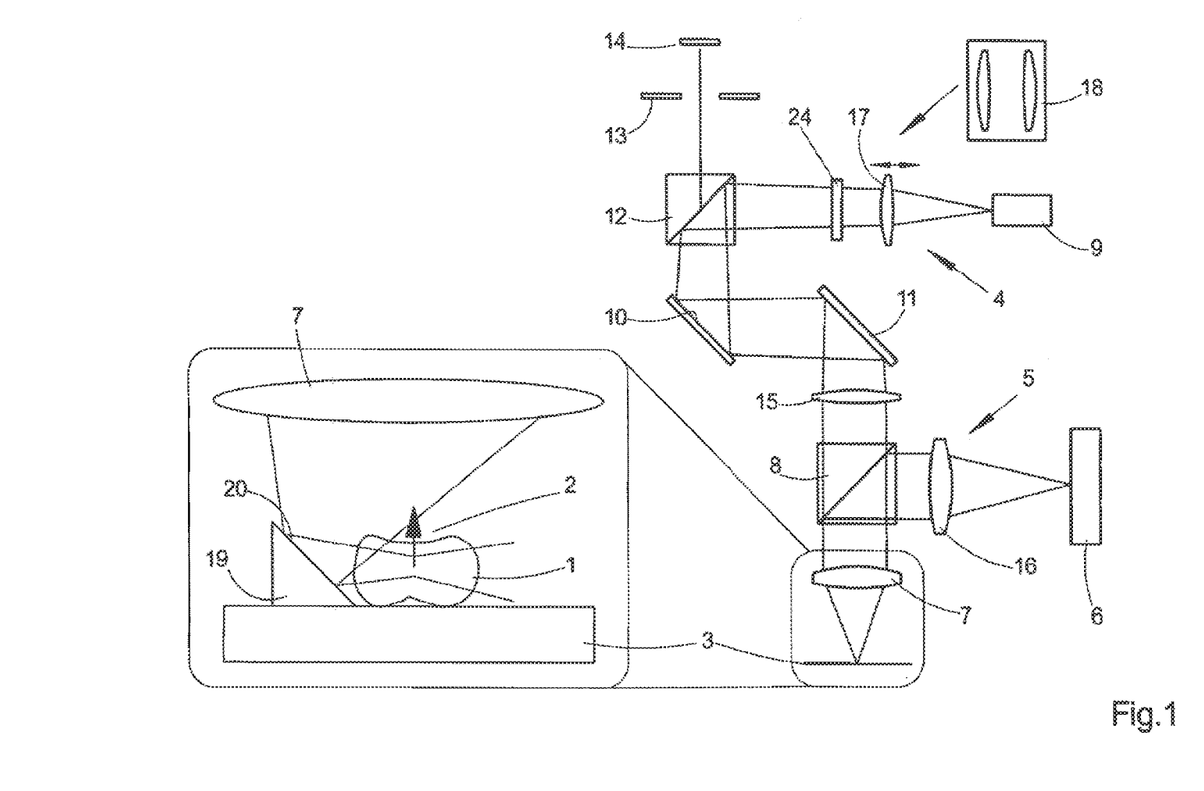
FIG. 1 shows a schematic diagram showing the overall construction of a microscope with light sheet illumination.

First, FIG. 1 shows the basic construction of a microscope with which a sample 1 can be irradiated with a light sheet perpendicular to the detection direction 2. A microscope of this type comprises a conventional sample stage with a stage surface in a stage plane perpendicular to an optical axis Z corresponding to the detection direction. The stage plane can also have another angle different than zero relative to the optical axis Z. A sample carrier 3 with a sample 1 is supported on the stage surface. The sample carrier 3 is not a sample chamber which is often used in SPIM studies, but rather a carrier which can be supported or fixed on conventional sample stages of microscopes for standard or inverted microscopy, It can also be a commercially available sample carrier.

The microscope has an excitation beam path 4 via which the sample 1 is illuminated with excitation light and a detection beam path 5 via which detection light coming from the sample I is directed to detection means. In the depicted example, the detection means comprise a conventional digital camera 6, for example with a CCD chip or CMOS chip for recording intensities. Fluorescence can be excited in fluorophores present in the sample 1, for example, via the excitation beam path 4 and this fluorescence can then be detected via the detection beam path 5. The microscope further comprises an objective 7 which is arranged along the optical axis and through which excitation light is directed toward the sample stage or sample carrier 3 and detection light coming from the sample 1 is directed toward the detection means. To separate the excitation light and detection light, the microscope further comprises beamsplitting means, in this case, beamsplitter 8, which can be constructed as an optical polarizing beamsplitter or as a dichroic mirror.

Finally, the microscope also comprises means for generating a light sheet from excitation light and means for illuminating the sample 1 with this light sheet. The light sheet lies in a plane which forms an angle different from zero with the optical axis Z. The excitation light itself originates from a laser 9 which can be a narrowband or broadband laser or a tunable laser with which the fluorophores present in the sample can be excited in particular. Single-photon processes and multiphoton processes are conceivable, also in combination. It is also possible to connect a plurality of lasers together.

In the depicted example, the microscope is formed as a laser scanning microscope. The means for generating the light sheet therefore comprise scanning means for scanning the sample which are constructed in this case as scanner mirrors 10 and 11 by which a point-shaped beam can be scanningly deflected over the sample in X direction and in Y direction clueing operation as scanning microscope. In the present example, scanner mirror 10 by which a line scanning can be realized is sufficient in principle. In an advantageous manner, however, both mirrors 10, 11 can also be used in conjunction in order to utilize both scanning directions and thus position the beam two-dimensionally Also, a simple stack recording can be realized in this manner. Further, the orientation of the scanning line and, therefore, of the quasi light sheet is freely selectable and can also result from a combined movement of the two scanner mirrors 10, 11.

Because of the high speed of the scan, a light sheet is generated effectively, i.e., temporally and spatially averaged. Instead of using a scanning microscope, the means for generating the light sheet can also be configured such that a static light sheet is generated, in which case the means for generating the light sheet comprise a cylindrical lens, for example.

In the depicted example, yet a further beamsplitter 12 is contained in the excitation beam path. This further beamsplitter 12 serves to optionally allow an additional confocal detection, for which purpose a pinhole 13 and a further detector 14 are arranged downstream of the beamsplitter 12. By appropriate actuation of the beamsplitter 8 and scanner mirrors 10 and 11, for example, it is possible in this way to switch back and forth between confocal detection and SPIM process. Tube lenses 15 and 16 serve for beam shaping in the excitation beam path 4 and detection beam path 5.

Figure 2:
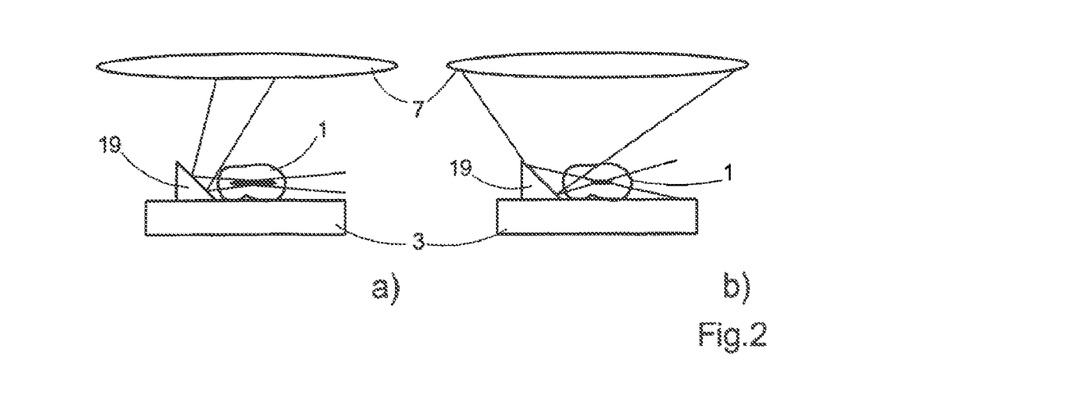

The focus of the light sheet can be positioned axially, i.e., relative to the optical axis Z in the plane of the light sheet, by means of collimation optics 17 in the excitation beam path 4. These collimation optics 17 can be supplemented or substituted by zoom optics 18, The pupil illumination can be varied with the latter and, therefore, the light sheet thickness and the divergence of the light sheet can be influenced. This is shown in two different illuminations in FIGS. 2a and 2b.

Further, at least one separate beam-shaping element 24 can be additionally arranged in the beam path. This separate beam-shaping element 24 can be configured, for example, as a phase-modulating element or a spatial modulator for light (spatial light modulator, SLM). By means of beam-shaping. elements of this kind, various beam shapes—for example, Bessel beams—can be adjusted for generation of light sheets. Optics based on micromirror actuators (digital micromirror device, DMD) can also be used as beam-shaping element 24 if parallel beam patterns are to be adjusted, for example.

Figure 3:
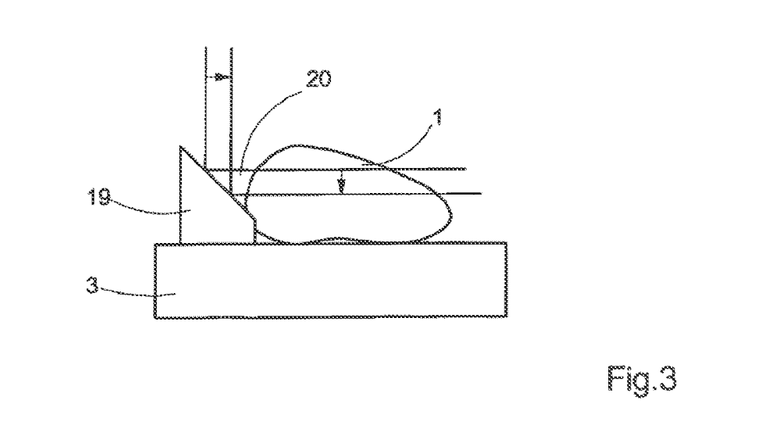
FIG. 3 shows the scanning of a sample in Z direction.

When using a laser scanning microscope for generating the light sheet, the second scanner mirror 11 can be used to vary the position of the scanning line relative to the optical axis so that the light sheet is displaced along Z direction by means of the optical deflecting device such that the sample can be scanned in a plurality of layers. A three-dimensional image of the sample can also be reconstructed from the data acquired in this way. The scanning of the sample in Z direction is illustrated by way of example in FIG. 3.

The means for illuminating the sample particularly comprise at least one optical deflecting device which is arranged on or at the sample carrier 3 and is configured to deflect excitation light coming from the objective 7 into the plane of the light sheet by means of at least one optically active surface, The at least one optical deflecting device is preferably configured in such a way that it deflects the excitation light at an optically active surface into a light sheet which lies in a plane forming a right angle with the optical axis Z. In this case, that is, the entire aperture area of the objective 7 can be used for detection, since the detection direction Z is then everywhere perpendicular to the light sheet plane.

In the example shown in FIG. 1, the at least one optical deflecting device is formed as mirror element 19, and the optically active surface is then formed as mirror surface 20. In order to generate a light sheet perpendicular to the detection direction Z, the at least one mirror surface 20 of mirror element 19 forms an angle of 45° to the optical axis Z in this case. Depending on beam guidance, however, other angles can also be used. The mirror element 19 is formed in this case by a planar mirror surface. When using at least two scanning means such as scanner mirrors 10, 11, the mirror element 19 can also be oriented in principle rotationally symmetrically with respect to the optical axis for example, in the shape of a conical frustum or a well in the sample carrier, since the position of the light sheet can be correspondingly adjusted through the use of at least two scanning mirrors. Adjustment of the position of the light sheet in the plane perpendicular to the detection direction Z can be provided for by means of additional adjusting means such as wobble plates. The mirror element 19 may simply be placed on the sample carrier 3, but can also be permanently or detachably connected thereto. In this case, commercially available sample carriers 3 can be used. One conceivable variant is also an integral manufacture of special sample carriers which are already provided with mil-tor elements 19. The mirror surface may be generated by vacuum deposition for example.

Optical deflecting devices formed as prism elements in which the optically active surface is formed as inner side of the prism ate especially suitable for inverted microscopy. The optically active surface can also be composed of a plurality of microprisms such that the reflecting or refracting surface is not directly tangent so as to prevent contaminations, for example, through solutions in which the sample is contained.

The arrangement of the optical deflecting devices is not limited to configuration as mirror element 19 or as prism element. Various possibilities for realizing optical deflecting devices are shown by way of example in FIGS. 4a) to 4d).

Figure 4:
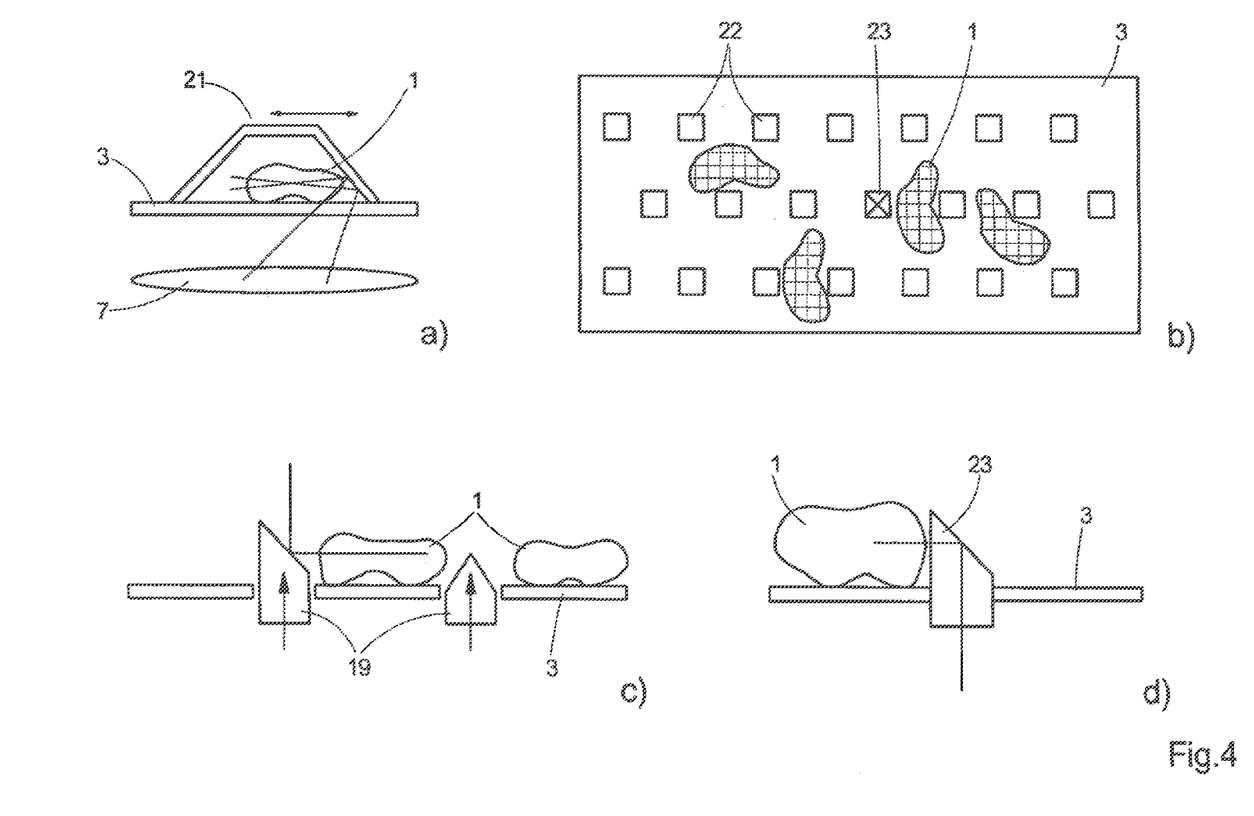

For example, the optically active surface of the at least one optical deflecting device can be formed so as to surround the sample in a funnel-shaped manner. FIG. 4a shows an example of this type. In this case, the optical deflecting device is formed such that it can be placed on the stage from above, for example in the form of a structure with a funnel-shaped optically active surface surrounding the sample. The optical deflecting device is shaped like a cap 21 in this case. This type of optical deflecting device is particularly suitable for inverted microscopy. In this case, the inner lateral walls of the cap 21 are mirrored or partially outfitted with mirrors, for example. Funnel-shaped structures of this kind have the advantage that they can be placed at any location on the sample stage, i.e., wherever'a sample is located, which is advantageous particularly with very small samples of individual cell structures. Subsequently, a corresponding orientation of the microscope and excitation light is carried out. The funnel-shaped structure can also be open at the top. It can have a plurality of lateral walls or an individual lateral wall, for example, a round lateral wall. When the funnel-shaped structure has a plurality of planar lateral walls, only one of them need be mirrored. On the other hand, in case of a true rotationally symmetrical funnel. shape, a quasi light sheet in the detection plane is conceivable, for example also by means of a combined movement of the scanner mirrors 10 and 11 such that a circular scan is carried out.

If the mirror surfaces of the caps 21 do not form an angle of 45° with the surface of the sample carrier 3, the light sheet is consequently not oriented perpendicular to the optical axis Z or not parallel to the surface of the sample carrier 3, particularly when the caps are formed of a flexible material. In this case, it is advantageous to provide adjusting means, for example a wobble plate or mirror, by means of which the angle of incidence of the excitation light on the mirrored surfaces can be varied to position the light sheet in a parallel manner.

Instead of positioning funnel-shaped structures on a plane surface of the sample carrier 3, the sample carrier 3 can also have at least one well which is preferably funnel-shaped. The above-mentioned shape variations for the funnel-shaped structures also apply in an analogous manner for these wells. At least one lateral wall is then incorporated in a well of this type, and this at least one lateral wall corresponds to the optically active surface. For inverted observation, this optically active surface takes over the function of the prism surface which directs light through the sample carrier 3. in case of illumination and detection from above the sample, the lateral walls can be mirrored. The caps and the wells can have different cross-sectional shapes, for example they can be round or square. Sample carriers with funnel-shaped wells are especially suitable for studying the growth of individual cells because the latter then remain limited to a relatively confined space, namely the funnel-shaped well. Alternatively or by way of supplementation, it is also possible to arrange a plurality of optical deflecting devices on the sample carrier 3, for example in the shape of a grid. A variant of this kind is shown in FIG. 4b). Here a plurality of optical deflecting devices are arranged in the form of prism elements 22 and 23, viscous samples 1 being located therebetween. Prism elements 22 are inactive and only prism element 23, identified by the cross, is active, i.e., illuminated, in order to generate a light sheet by means of this prism element 23 and to examine the sample adjacent to this prism element 23. The optical deflecting devices need not be arranged on the sample carrier 3 from the start. In the arrangement shown in FIG. 4c), the optical deflecting devices which are again formed in this case as mirror elements 19 can be introduced into corresponding openings in the sample carrier from below relative to the sample carrier along the optical axis. This is indicated by the perpendicular arrows. In so doing, a sieve structure can be predetermined in the sample carrier 3, but it is also conceivable that the openings for the optical deflecting devices are first punched through the latter when inserted.

Finally, FIG. 4d) shows the use of a prism element 23 in which the optically active surface is formed of microprisms. In this way, the reflecting surface does not enter in direct contact with the surrounding liquid, and the surface is not contaminated.

Figure 5:
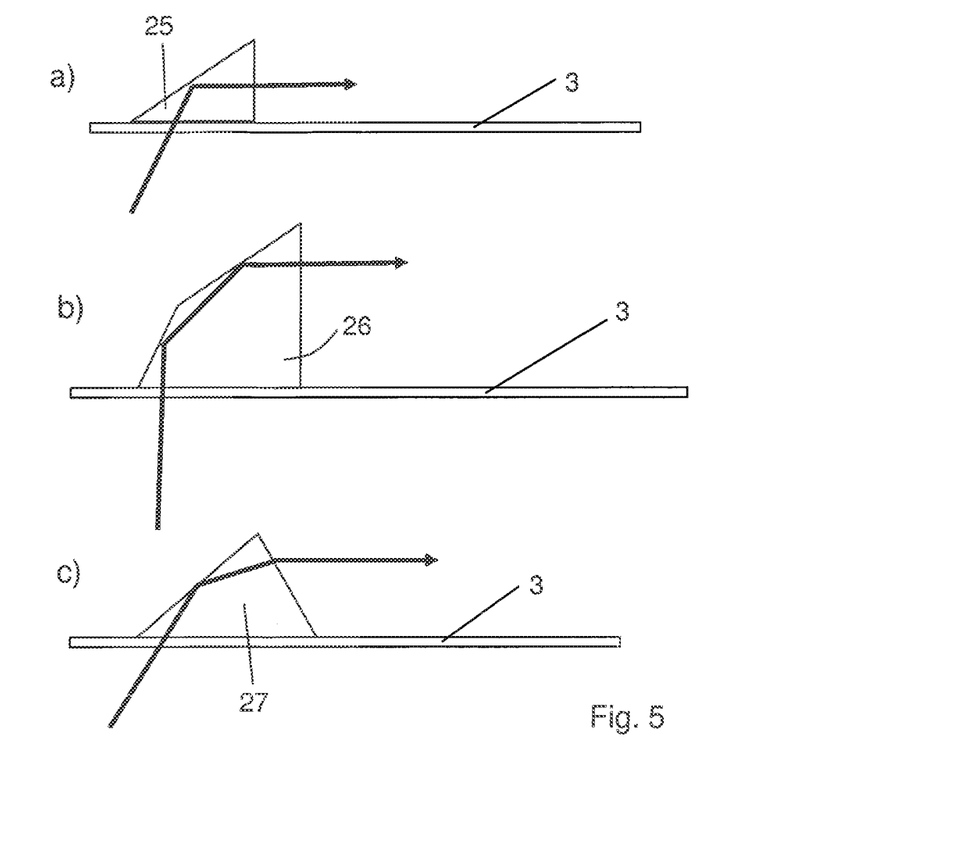

FIGS. 5a)-c) show a further embodiment of the at least one optical deflecting device with an optically active surface as microprisms. While the optical deflecting devices 22, 23 shown in FIGS. 4b) and 4d) have microprisms with mirrored surfaces, a mirroring of this kind can be dispensed with in the arrangements shown in FIG. 5 because the principle of total reflection is made use of in this case, which acts equivalently to a mirroring of surfaces insofar as the corresponding boundary conditions are met. In so doing, the optically active surfaces also need not necessarily be formed as microprisms. The necessary conditions for the occurrence of total reflection can also be initiated with polished surfaces.

Overwhelmingly, samples, particularly cells, are examined in aqueous solution so that the use of optical deflecting devices having optically active surfaces in the configuration that is advantageous for mirrored surfaces and which form an angle of 45° with the optical axis -Z cannot readily be used because of the ratio of the refractive index—1.33 for water and, e.g., 1.52 for glass or plastic. Rather, the angle must be about 60° in order to make use of total reflection at the water-glass interface. FIGS. 5a)-c) show three possibilities for configuring optical deflecting devices working on the principle of total reflection under such conditions.

FIG. 5a) shows a prism element 25 in which the optically active surface forms an angle of 45° with the optical axis Z on the average. However, the microprisms or optically active surface are/is not mirrored. The beam of excitation light does not, however, impinge in the optical deflecting devices parallel to the optical axis as in the examples described above; rather, the optical axis forms an angle different than zero such that the conditions for total reflection are met at the optically active surface.

In the arrangement shown in FIG. 5a), however, the numerical aperture of the excitation light is impaired compared to a configuration with perpendicular light incidence. Therefore, FIG. 5b) shows another arrangement in which the light incidence can continue to be carried out perpendicularly, wherein however specially configured prism elements 26 must be used in which the deflection takes place at a shallower angle and which are provided with a plurality of optically active surfaces, Finally, in the arrangement shown in FIG. 5c), the beam of excitation light is likewise guided into a prism element 27 at an angle to the optical axis Z that is different than zero. The excitation light undergoes total reflection at a first optically active surface based on microprisms and is refracted at a second optically active surface so that ultimately a light sheet is again generated which forms an approximately right angle with the optical axis Z.

The device described above uses one and the same objective for generating the light sheet and for detection, which is an essential prerequisite for integrating in existing microscopes. Further, by decoupling the optical deflecting device from the objective 7 and coupling to the sample carrier 3, a light sheet which lies in a plane perpendicular to the detection direction Z can be generated economically. In particular, the configurations of the optical deflecting devices advantageously allow very small and extremely small samples on the magnitude of individual cells to be analyzed. Combining with laser scanning methods, PALM methods or with numerous other methods is possible. Image stacks of the sample can be generated from different sections in Z direction by means of displacing the sample carrier 3 in die stage plane or scanning plane of the light sheet.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

LIST OF REFERENCE NUMERALS 1 sample
2 detection device
3 sample carrier
4 excitation beam path
5 detection beam path
6 camera
7 objective
8 beamsplitter
9 laser
10, 11 scantier mirrors
12 beamsplitter
13 pinhole
14 detector
15, 16 tube lens
17 collimation optics
18 zoom optics
19 mirror element 20 mirror surface
21 cap
22 inactive prism element
23 active prism element
24 beam-shaping element

The invention claimed is:

1. A microscope arrangement comprising:
 a sample stage comprising:
  a stage surface in a stage plane which forms an angle different than zero to an optical axis; and
  a sample carrier configured to hold a sample, the sample carrier being supported on the stage surface;
 an excitation beam path configured to illuminate the sample with excitation light when the sample is arranged on the sample carrier;
 a detection beam path configured to direct detection light coming from the sample to detection means;
 an objective which is arranged along the optical axis and through which the excitation light is guided in direction of the sample stage and the detection light coming from the sample is guided in direction of the detection means;
 a beam-splitting means configured to separate excitation light and detection light;
 a means for generating a light sheet from the excitation light;
 a means for illuminating the sample with the light sheet;
 wherein the light sheet lies in a plane which forms an angle different than zero to the optical axis;
 wherein the means for illuminating the sample comprises a plurality of optical deflecting devices which is arranged on the sample carrier and which is configured to deflect the excitation light coming from the objective into the plane of the light sheet by means of at least one optically active surface.

2. The microscope arrangement according to claim 1; wherein the plurality of optical deflecting devices is formed so as to deflect the excitation light at at least one optically active surface into a light sheet which lies in a plane forming an angle different than zerowith the optical axis.

3. The microscope arrangement according to claim 2; wherein the optically active surface is formed in a funnel-shaped manner so as to at least partially surround the sample.

4. The microscope arrangement according to claim 1; wherein at least one optical deflecting device of the plurality of optical deflecting devices is configured as a mirror element with at least one optically active surface formed as a mirror surface.

5. The microscope arrangement according to claim 4; wherein the at least one mirror surface forms an angle of 45° with the optical axis.

6. The microscope arrangement according to claim 1; wherein at least one optical deflecting device of the plurality of optical deflecting devices is configured as a prism element with an optically active surface which is formed as an inner side of a prism.

7. The microscope arrangement according to claim 6; wherein the optically active surface forms an angle of 45° with the optical axis.

8. The microscope arrangement according to claim 1; wherein the at least one optically active surface is comprised of a plurality of microprisms.

9. The microscope arrangement according to claim 8; wherein the optically active surface on average forms an angle of 45° with the optical axis.

10. The microscope arrangement according to claim 1: wherein the sample carrier comprises an opening configured to receive at least one optical deflecting device of the plurality of optical deflecting devices.

11. The microscope arrangement according to claim 1; wherein the plurality of optical deflecting devices comprises a structure configured to be placed on the sample carrier or on the sample stage so as to surround the sample with a funnel-shaped optically active surface.

12. The microscope arrangement according to claim 1; wherein at least one optical deflecting device of the plurality of optical deflecting devices is detachably outfitted with a protective device configured to protect the deflecting device when culturing and/or transporting.

13. The microscope arrangement according to claim 1; wherein the sample carrier comprises at least one well with at least one lateral wall; and
 wherein the at least one lateral wall corresponds to the optically active surface.

14. The microscope arrangement according to claim 1; wherein an adjusting means configured to adjust the light sheet is arranged in the excitation beam path.

15. The microscope arrangement according to claim 1; wherein the microscope is formed as a laser scanning microscope, and the light sheet is generated by a scanning means for point scanning.

16. The microscope arrangement according to claim 15; wherein the scanning means for point scanning comprises at least one scanner mirror.

17. The microscope arrangement according to claim 1, further comprising:
 zoom optics arranged in the excitation beam path and configured to vary the thickness of the light sheet.

18. The microscope arrangement according to claim 1, further comprising:
 collimation optics arranged in the excitation beam path and configured to position the focus of the light sheet relative to the optical axis.

19. The microscope arrangement according to claim 1, further comprising:
 a beam-shaping element arranged in the excitation beam path and configured to vary a shape and/or a structure of the light sheet.

* * * * *